(12) United States Patent
Shirota

(10) Patent No.: US 10,987,074 B2
(45) Date of Patent: Apr. 27, 2021

(54) RADIATION IMAGE CAPTURING APPARATUS

(71) Applicant: Shimadzu Corporation, Kyoto (JP)

(72) Inventor: Ken Shirota, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 92 days.

(21) Appl. No.: 15/763,482

(22) PCT Filed: Dec. 10, 2015

(86) PCT No.: PCT/JP2015/084633
§ 371 (c)(1),
(2) Date: Mar. 27, 2018

(87) PCT Pub. No.: WO2017/098626
PCT Pub. Date: Jun. 15, 2017

(65) Prior Publication Data
US 2018/0271462 A1    Sep. 27, 2018

(51) Int. Cl.
*A61B 6/04* (2006.01)
*A61B 6/00* (2006.01)

(52) U.S. Cl.
CPC .............. *A61B 6/4476* (2013.01); *A61B 6/00* (2013.01); *A61B 6/4021* (2013.01);
(Continued)

(58) Field of Classification Search
CPC .... A61B 6/00; A61B 6/02; A61B 6/40; A61B 6/405; A61B 6/42; A61B 6/4233;
(Continued)

(56) References Cited

U.S. PATENT DOCUMENTS

| 2012/0059239 | A1 | 3/2012 | Yamaguchi |
| 2013/0077744 | A1* | 3/2013 | Kamiya ............... A61B 6/5241 378/62 |

(Continued)

FOREIGN PATENT DOCUMENTS

| CN | 103516973 A | 1/2014 |
| JP | 2012-55475 A | 3/2012 |
| WO | 2015/146526 A1 | 1/2015 |

OTHER PUBLICATIONS

Extended European Search Report in corresponding application EP 15 91 0242, dated Apr. 8, 2019.

(Continued)

*Primary Examiner* — David P Porta
*Assistant Examiner* — Mamadou Faye
(74) *Attorney, Agent, or Firm* — Muir Patent Law, PLLC

(57) ABSTRACT

A radiation image capturing apparatus maintains previous image capturing position data stored in an image capturing position data storage unit 15 of a control unit 13 when a setting of a reference position of a long-length imaging region and the number of images to be captured are not changed. On the other hand, the radiation image capturing apparatus clears the previous image capturing position data stored in the image capturing position data storage unit 15 of the control unit 13 when either a setting of a reference position of a long-length imaging region or the number of images to be captured is changed. Then, the control unit 13 temporarily prohibits X-ray image capturing, and a warning display unit 16 causes a display unit 11 to display a display prompting input of image capturing position data for subsequent long-length image capturing. This display is kept displayed until an operator inputs image capturing position data for subsequent long-length image capturing. When an operator inputs image capturing position data for the subsequent long-length image capturing and the data is stored in (Continued)

the image capturing position data storage unit 15 of the control unit 13, the control unit 13 releases the prohibition of image capturing.

12 Claims, 7 Drawing Sheets

(52) U.S. Cl.
CPC ............ *A61B 6/4452* (2013.01); *A61B 6/461* (2013.01); *A61B 6/545* (2013.01); *A61B 6/5241* (2013.01)

(58) Field of Classification Search
CPC ......... A61B 6/4417; A61B 6/44; A61B 6/505; A61B 6/54; A61B 6/544; G01N 23/083
See application file for complete search history.

(56) References Cited

U.S. PATENT DOCUMENTS

2013/0336456 A1    12/2013  Tanaka
2016/0220219 A1*   8/2016  Lalena ................... A61B 6/545

OTHER PUBLICATIONS

First Chinese Office Action dated Jan. 11, 2021 for the corresponding Chinese Patent Application No. 201580085048.X, submitted with a machine translation.

* cited by examiner

| No. | Image capturing menu | Tube voltage | Tube current | Image capturing time | Reference position | The number of images to be captured |
|---|---|---|---|---|---|---|
| 1 | Entire spinal front image | 85 kV | 250 mA | 100 msec | None | 2 images |
| 2 | Entire spinal side image | 95 kV | 250 mA | 100 msec | None | 2 images |
| 3 | Entire spinal side image | 95 kV | 250 mA | 100 msec | None | 3 images |
| 4 | Entire lower limb front image | 80 kV | 200 mA | 100 msec | Lower | 3 images |
| 5 | Entire lower limb front image | 90 kV | 200 mA | 100 msec | Lower | 3 images |

FIG. 6

RADIATION IMAGE CAPTURING APPARATUS

TECHNICAL FIELD

The present invention relates to a radiation image capturing apparatus, and more particularly to a radiation image capturing apparatus that performs long-length image capturing of a subject along a body axis direction thereof by composing a plurality of images.

BACKGROUND ART

Conventionally, as a method for creating an X-ray image of a long-length image capturing region of a subject extending in a body axis direction thereof, such as, e.g., an entire spinal image and an entire lower limb image, an X-ray image capturing apparatus is known in which a long-length X-ray image is created by capturing a plurality of rectangular images along a longitudinal direction of a subject by irradiating an X-ray toward a moving X-ray detection unit by moving an X-ray tube while moving the X-ray detection unit along the longitudinal direction of the subject and composing these images.

Patent Document 1 discloses a radiation image capturing apparatus. According to the radiation image capturing apparatus, in the case of performing such a long-length image capturing, when a body motion of a subject is detected, re-image capturing assist information for assisting re-image capturing of a radiographic image is displayed, so that an operator can perform the re-image capturing so as not to cause a body motion by performing the image capturing in accordance with the re-image capturing assist information.

PRIOR ART DOCUMENT

Patent Document

Patent Document 1: Japanese Unexamined Patent Application Publication No. 2012-55475

SUMMARY OF THE INVENTION

Problems to be Solved by the Invention

In the case of performing such long-length image capturing, image capturing conditions are set in advance according to an image capturing menu. FIG. 6 is a table showing image capturing conditions set according to image capturing menus. Note that more image capturing conditions are set actually, but in FIG. 6, five kinds of image capturing conditions are set for the sake of convenience of explanation.

As shown in this table, for example, in the case of capturing an entire spinal front image indicated by No. 1 and in the case of capturing an entire spinal side image indicted by No. 2, the tube voltages are set to be different from each other because the body thicknesses are different from each other although the number of images to be captured is the same. In the case of capturing the entire spinal image indicated by No. 1 and No. 2 and in the case of capturing the entire lower limb image indicated by No. 4 and No. 5, the number of images to be captured is different from each other, and in the lower limb image capturing, it is preferable to capture the image from the lower end region of the lower limb as low as possible. Therefore, a lower reference in which the image capturing reference position is set to a lower position is adopted, and the upper end position of the image capturing is set with reference to the lower reference. On the other hand, in the case of capturing an entire spinal image, the upper end position and the lower end position of the image capturing are set according to a height of a subject.

Also in the case of capturing images of the same part from the front and the side, in some cases, the number of images to be captured is changed. FIG. 7 is an explanatory view showing a state in which the number of images to be captured differs between the case in which the image capturing is performed from the front and the case in which the image capturing is performed form the side as described above.

FIG. 7 shows a case of capturing an entire spinal image of a subject M in order to diagnose the spinal distortion of the subject M. In the case of performing such image capturing, when capturing the image of the subject M from the front, it may be sufficient to capture two images of the entire spine. On the other hand, in the case of performing the image capturing of the subject M from the side, it is necessary to know the position of the center of gravity in order to diagnose the distortion of the spine, so it is necessary to capture five (5) images from the spine to the heel of the subject M. At this time, in order to reduce the exposure dose to the subject M by reducing the number of images to be captured, in some cases, a lead plate 90 is placed at the position on the extension line from the heel, and three images are captured from the spine of the subject M to the lead plate 90. In either of the cases, the number of images to be captured will be different between the case in which the image capturing is performed from the front and the case in which the image capturing is performed from the side. Note that the case of performing image capturing of two images from the front of the subject M and the case of performing image capturing of three images from the side thereof are indicated by No. 1 and No. 3 in FIG. 6, respectively.

As described above, in the case of performing an entire spinal image capturing, it is necessary to set an upper end position and a lower end position of an image capturing region according to a height of a subject M. Also, in the case of performing an entire lower limb image capturing, it is necessary to set an upper end position of an image capturing region with respect to a reference position as a lower position. Therefore, in the case of performing long-length image capturing, it takes time to set the image capturing position. For example, in cases where presetting is adopted in which when setting a device, image capturing conditions are returned to initial settings every time the image capturing is performed, even in the case of continuously performing the image capturing of the same range from the front side or even in the case of re-performing the image capturing, it is necessary to reset the image capturing range. Further, in cases where the device has been set so that it takes over the previous image capturing conditions, for example, in cases where the image capturing indicated by No. 1 is performed, followed by the image capturing indicated by No. 4 shown in FIG. 6, it is necessary to perform operations of setting the reference position to a lower position, setting the number of images to be captured to three (3), and setting the upper end position of the image capturing region. This may take a long time depending on the skill level of the operator.

Here, such long-length image capturing in a standing posture is image capturing which is often targeted to a subject M whose spine and/or lower limb are curved. Therefore, considering the burden on the subject M, it is preferable to complete the image capturing as quickly as possible. On the other hand, in the case of long-length image capturing, it is required to consecutively perform image capturing a plurality of times, and therefore the time required for the image capturing becomes several times as compared with ordinary image capturing. Considering the above, it is preferable to set the time required for setting the image capturing position at the time of performing long-length image capturing as short as possible.

The present invention was made to solve the above problems, and aims to provide a radiation image capturing apparatus capable of efficiently performing long-length image capturing by omitting unnecessary settings of an image capturing position at the time of performing the long-length image capturing.

Means for Solving the Problems

According to the invention as recited in claim 1, a radiation image capturing apparatus equipped with a radiation detection unit configured to move along a body axis direction of a subject and a radiation irradiation unit configured to irradiate radiation toward the radiation detection unit, wherein the radiation image capturing apparatus is configured to perform long-length image capturing for creating a radiation image corresponding to a long-length image capturing region of a subject extending in a body axis direction of the subject by continuously performing image capturing a plurality of times to capture a plurality of images in which end portions thereof are overlapped and composing the plurality of images, characterized in that the radiation image capturing apparatus is equipped with a control unit, the control unit is configured to maintain image capturing position data for previous long-length image capturing when a setting of a reference position of the long-length image capturing region is not changed and the number of images to be captured are not changed after performing the previous long-length image capturing and before performing next long-length image capturing, and the control unit is configured to clear the image capturing position data for the previous long-length image capturing and prohibit the next long-length image capturing until image capturing position data for the next long-length image capturing is input when the setting of the reference position of the long-length image capturing region is changed or the number of images to be captured is changed after performing the previous long-length image capturing and before performing the next long-length image capturing.

According to the invention as recited in claim 2, in the invention as recited in claim 1, the control unit makes a display unit display a display prompting input of image capturing position data for the next long-length image capturing when the setting of the reference position of the long-length image capturing region is changed or the number of images to be captured is changed after performing the previous long-length image capturing and before performing the next long-length image capturing.

According to the invention as recited in claim 3, in the invention as recited in claim 1, a change of the setting of the reference position of the long-length image capturing region includes a change between a setting in which the reference position of the long-length image capturing region is set to a lower end portion of the subject and a setting in which the reference position of the long-length image capturing region is not set to the lower end portion of the subject.

According to the invention as recited in claim 4, in the invention as recited in any one of claims 1 to 3, the radiation detection unit is configured to move in a vertical direction and perform long-length image capturing of the subject in a standing position.

Effects of the Invention

According to the invention as recited in claim 1, since it is sufficient to perform a setting of the image capturing position only when it is necessary to reset the image capturing position, it becomes possible to efficiently perform long-length image capturing by omitting unnecessary settings of an image capturing position at the time of performing the long-length image capturing. This makes it possible to shorten the time required for the long-length image capturing.

According to the invention as recited in claim 2, the necessity of setting the image capturing position is displayed, which makes it possible to perform a prompt input operation.

According to the invention as recited in claim 3, when capturing the entire lower limb image and the entire spinal image for example, it is possible to efficiently perform changing of the image capturing position between an image capturing position as a lower reference and other image capturing positions.

According to the invention as recited in claim 4, it becomes possible to efficiently perform image capturing in a standing posture which is particularly heavy burden on a subject.

BRIEF DESCRIPTION OF THE DRAWINGS

FIG. 6 is a table showing image capturing conditions set according to image capturing menus.

EMBODIMENTS FOR CARRYING OUT THE INVENTION

Figure 1:
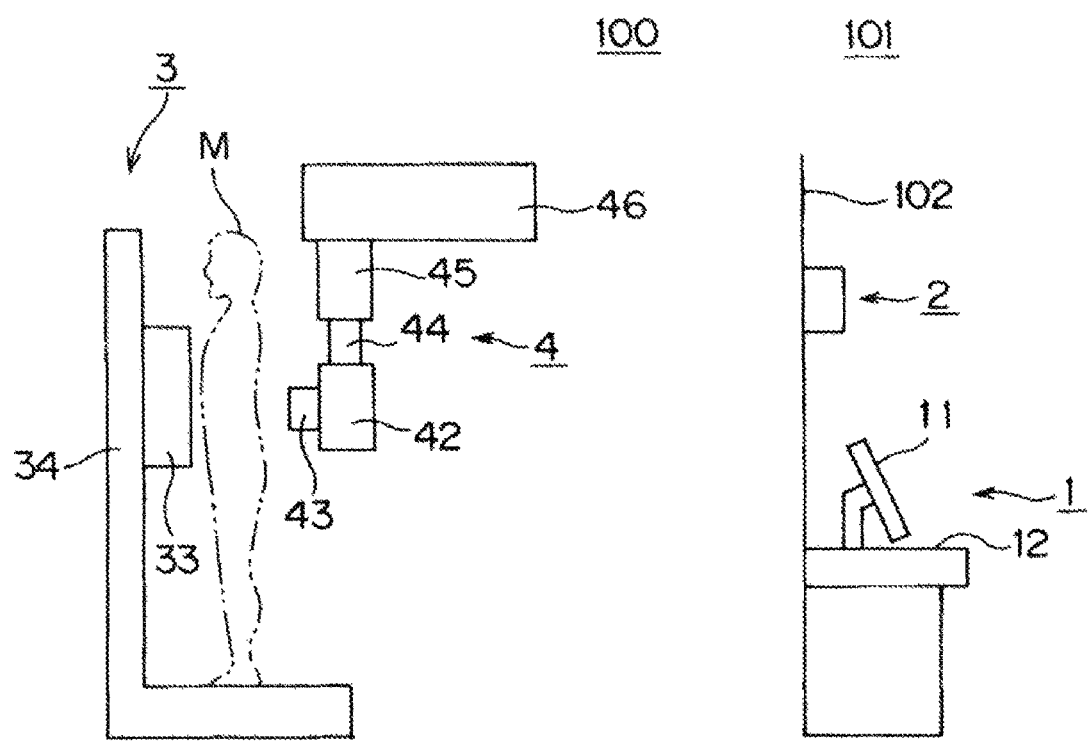
FIG. 1 is a schematic diagram of an X-ray image capturing apparatus as a radiation image capturing apparatus according to the present invention.
Figure 2:
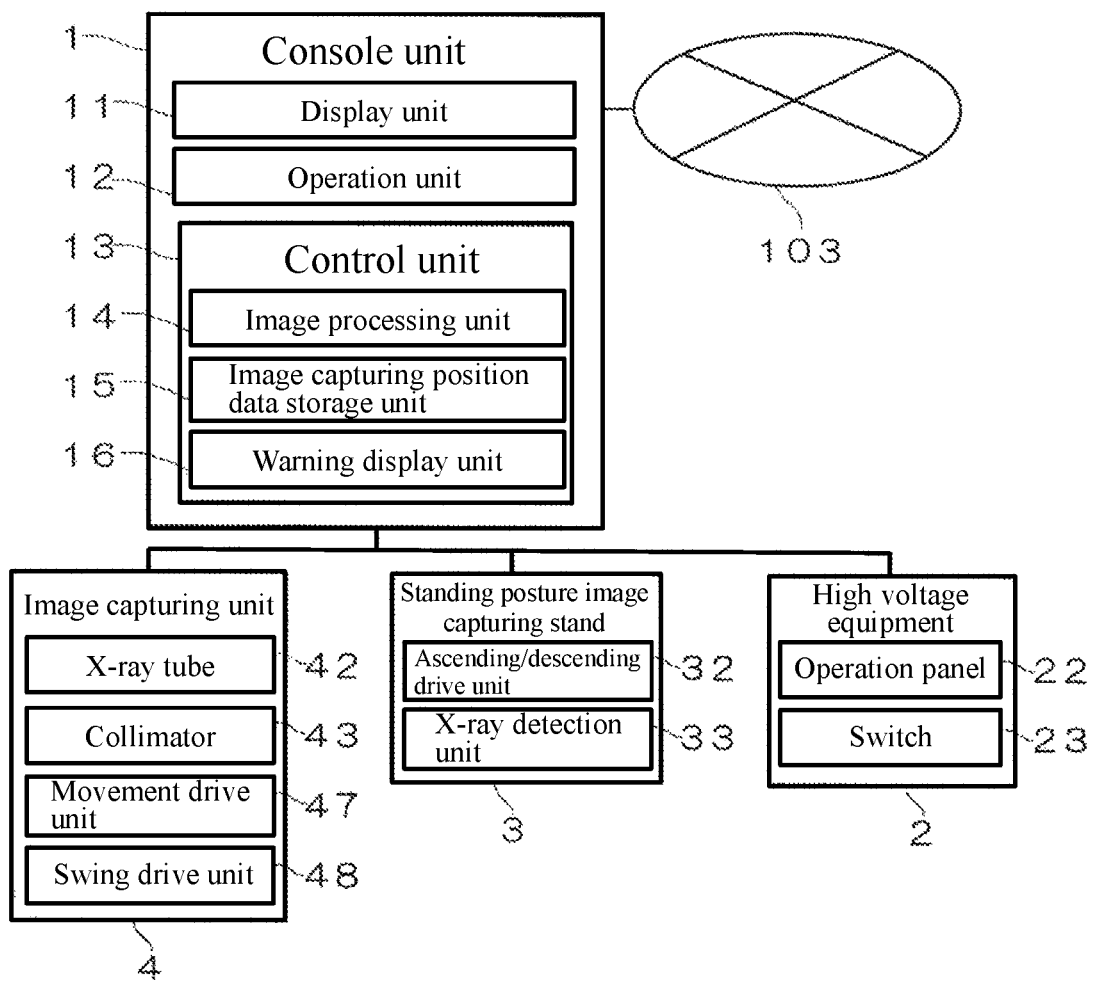
FIG. 2 is a block diagram showing a main control system of the X-ray image capturing apparatus according to the present invention.

Hereinafter, embodiments of the present invention will be described with reference to the drawings. FIG. 1 is a schematic diagram of an X-ray image capturing apparatus as a radiation image capturing apparatus according to the present invention. FIG. 2 is a block diagram showing a main control system of the X-ray image capturing apparatus according to the present invention.

The X-ray image capturing apparatus according to the present invention is equipped with a console unit 1 and a high voltage equipment 2, which are installed in an operation room 101 for an operator to perform an X-ray image capturing operation, and a standing posture image capturing stand 3 and an image capturing unit 4, which are installed in an image capturing room 100 for capturing an image of a subject M. The image capturing room 100 and the operation room 101 are shielded by a partition wall 102.

The console unit 1 is equipped with a display unit 11 composed of, e.g., a liquid crystal display and an operation unit 12 composed of, e.g., a keyboard and a mouse for performing various operations. The display unit 11 displays an X-ray captured image. Further, as shown in FIG. 2, the console unit 1 is equipped with a control unit 13 for controlling the entire device. This control unit 13 is equipped with an image processing unit 14 for performing various kinds of image processing including image compositing which will be described later, an image capturing position data storage unit 15 for temporarily storing image capturing position data at the time of the long-length image capturing, and a warning display unit 16 for displaying a display prompting input of image capturing position data on the display unit 11. As shown in FIG. 2, this console unit 1 is connected to a radiology department information system (RIS) 103, which is an in-hospital communication of a subject management system in a hospital.

The high voltage equipment 2 is mounted in the partition wall 102 in the operation room 101. As shown in FIG. 2, the high voltage equipment 2 is equipped with an operation panel 22 having a display unit, an input button, etc., constituted by a touch panel type liquid crystal display, etc., and a switch 23 for starting irradiation of an X-ray from the X-ray tube 42. This high voltage equipment 2 is for setting X-ray irradiation conditions, such as, e.g., a tube voltage and a tube current of the X-ray tube 42 or an X-ray irradiation time, or for changing the X-ray image irradiation conditions set based on the information from the radiology department information system 103 based on the X-ray image capturing conditions as necessary.

As shown in FIG. 1, the standing posture image capturing stand 3 is equipped with an ascending/descending unit 34 that supports the X-ray detection unit 33 in an ascendable and descendible manner. The X-ray detection unit 33 is also called a bucky unit, and is provided with an X-ray detector, such as, e.g., a flat panel detector (FPD) therein. As shown in FIG. 2, the standing posture image capturing stand 3 is equipped with an ascending/descending drive unit 32 for ascending/descending the X-ray detection unit 33 to thereby change the height position thereof. The X-ray tube 42 constitutes the radiation irradiation unit according to the present invention, and the X-ray detection unit 33 constitutes the radiation detection unit according to the present invention.

As shown in FIG. 1, the image capturing unit 4 is equipped with a base unit 46 movable in a direction orthogonal to the ceiling of the image capturing room 100, a support unit 45 extending downward from the base unit 46, and a movable unit 44 which ascends/descends and rotates with respect to the support unit 45. The movable unit 44 supports an X-ray tube 42 and a collimator 43. Therefore, the X-ray tube 42 and the collimator 43 are movable in an integrated manner. The X-ray tube 42 and the collimator 43 are integrally swingable with respect to the movable unit 44. As shown in FIG. 2, the image capturing unit 4 is equipped with a movement drive unit 47 for integrally moving the X-ray detection unit 33 and the collimator 43 by drivingly controlling a motor (not shown) and a swing drive unit 48 for swinging the X-ray tube 42 and the collimator 43 by controlling a motor (not shown).

Figure 3:
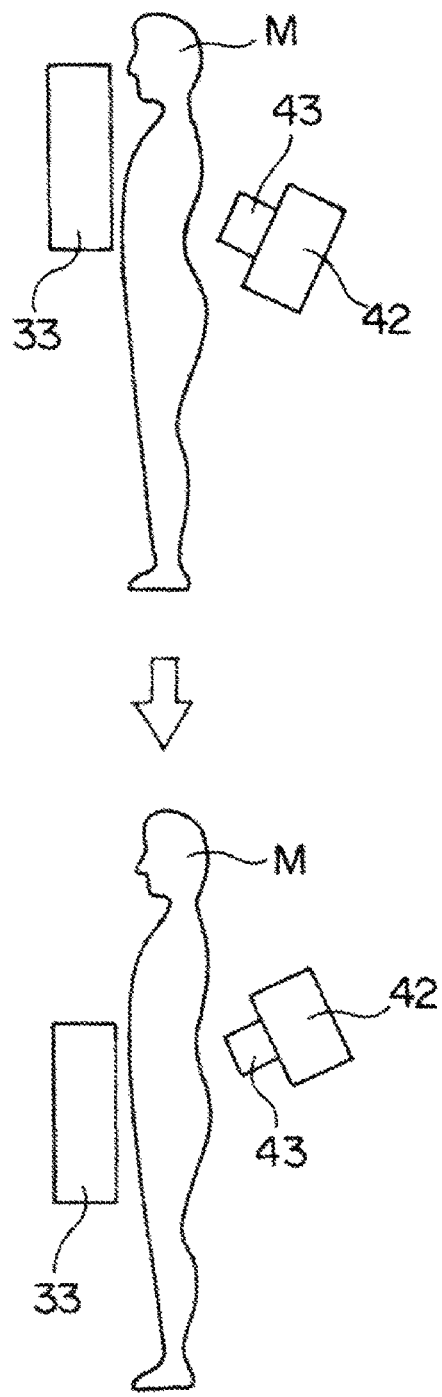
FIG. 3 is an explanatory diagram schematically showing a long-length image capturing operation.
Figure 4:
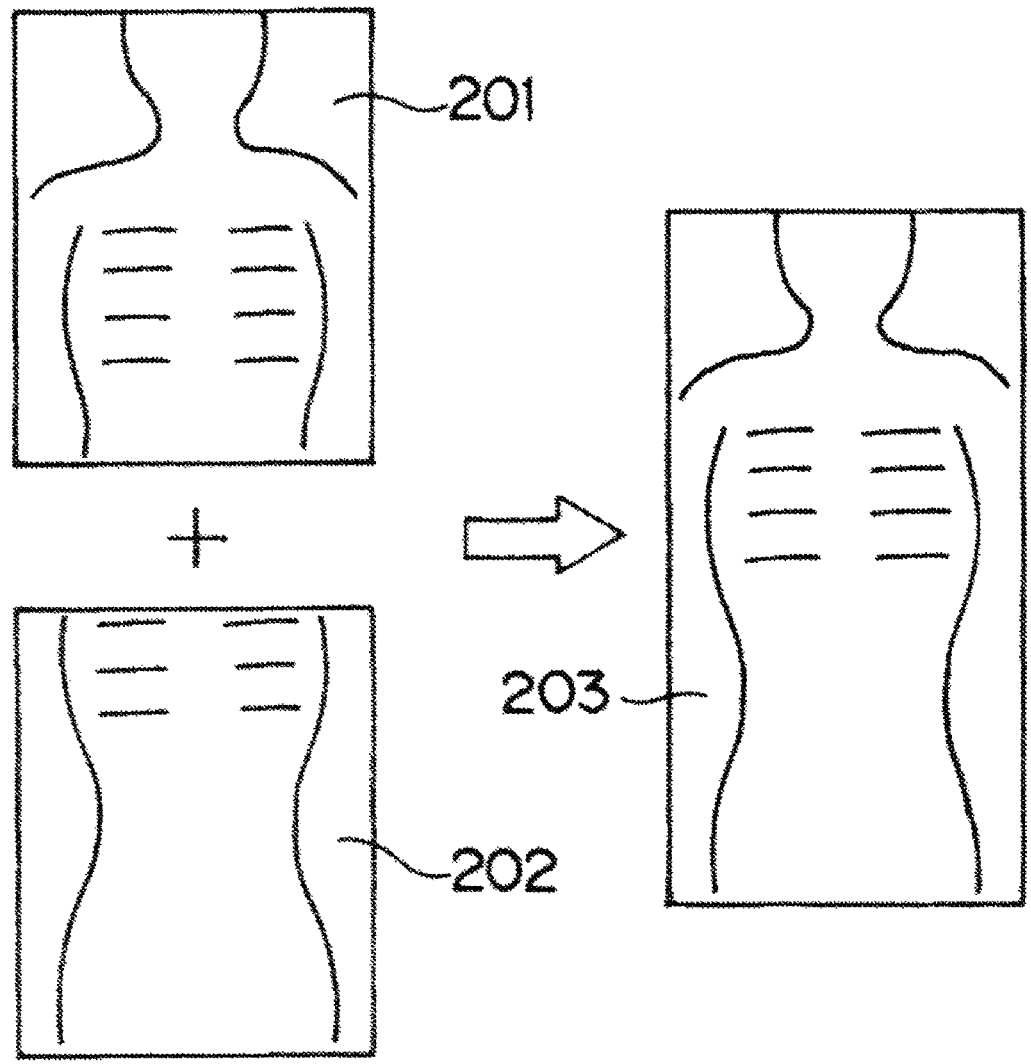
FIG. 4 is a schematic diagram showing an X-ray image obtained by the long-length image capturing operation.

Next, the basic operation for performing long-length image capturing by the above-mentioned X-ray image capturing apparatus will be described. FIG. 3 is an explanatory diagram schematically showing a long-length image capturing operation, and FIG. 4 is a schematic diagram showing an X-ray image obtained by the long-length image capturing operation. Note that FIG. 3 and FIG. 4 show that in the case of capturing an entire spinal image from the front as indicated by No. 1 in FIG. 6, the case in which a long-length X-ray image 203 is created by combining two X-ray images 201 and 202.

When long-length image capturing is performed, the upper end position of the long-length image capturing region is set. At this time, for example, a laser beam is irradiated from a laser light source attached to the collimator 43 toward the subject M to display a line by the laser beam on the body surface of the subject M, swing angle positions of the X-ray tube 42 and the collimator 43 are changed so as to indicate the upper end position of the long-length image capturing region using the laser beam line, and the swing angle positions at that time are stored. At the time of the X-ray image capturing, based on the data for the swing angle positions, the X-ray tube 42 and the collimator 43 are swung so that the upper end of the image capturing range coincides with the upper end of the long-length image capturing region. Instead of using the laser beam as described above, it may be configured such that the swing angle positions of the X-ray tube 42 and the collimator 43 are set so that the upper end of the image capturing range coincides with the upper end of the long-length image capturing region by using the light irradiation field by the collimator lamp.

Next, the X-ray tube 42 and the collimator 43 are swung downward by the swing drive unit 48 of the image capturing unit 4 shown in FIG. 2. Then, the lower end position of the long-length image capturing region is set by the same process as when setting the upper end position of the long-length image capturing region.

Upon completion of the settings of the upper end position and the lower end position of the long-length image capturing region, image capturing is started. At this time, first, the X-ray detection unit 33, the X-ray tube 42, and the collimator 43 are arranged at the positions shown on the upper side of FIG. 3, and the first X-ray image capturing is performed. With this, the X-ray image 201 shown in FIG. 4 is captured. Next, the X-ray detection unit 33, the X-ray tube 42, and the collimator 43 are arranged at the positions shown on the lower side of FIG. 3, and the second X-ray image capturing is performed. With this, the X-ray image 202 shown in FIG. 4 is captured.

These X-ray images 201 and 202 are transmitted to the control unit 13 of the console unit 1 shown in FIG. 2. Then, the image processing unit 14 in the control unit 13 composes two X-ray images 201 and 202 to create a long-length X-ray image 203 shown in FIG. 4.

In the case of performing the entire lower limb image capturing indicated by No. 4 or No. 5 in FIG. 6, not in the case of performing the entire spinal image capturing indicated by No. 1 in FIG. 6 as shown in FIG. 3 and FIG. 4, it is preferable to perform image capturing from the lower end portion region of the lower limb as low as possible. For this reason, the reference position of the image capturing is set to a lower position, and an upper end position of the image capturing is set based on the reference position. Therefore, in this case, it is only necessary to set the upper end position of the image capturing region with the reference position as the lower position by the same process as the above-described process.

Figure 5:
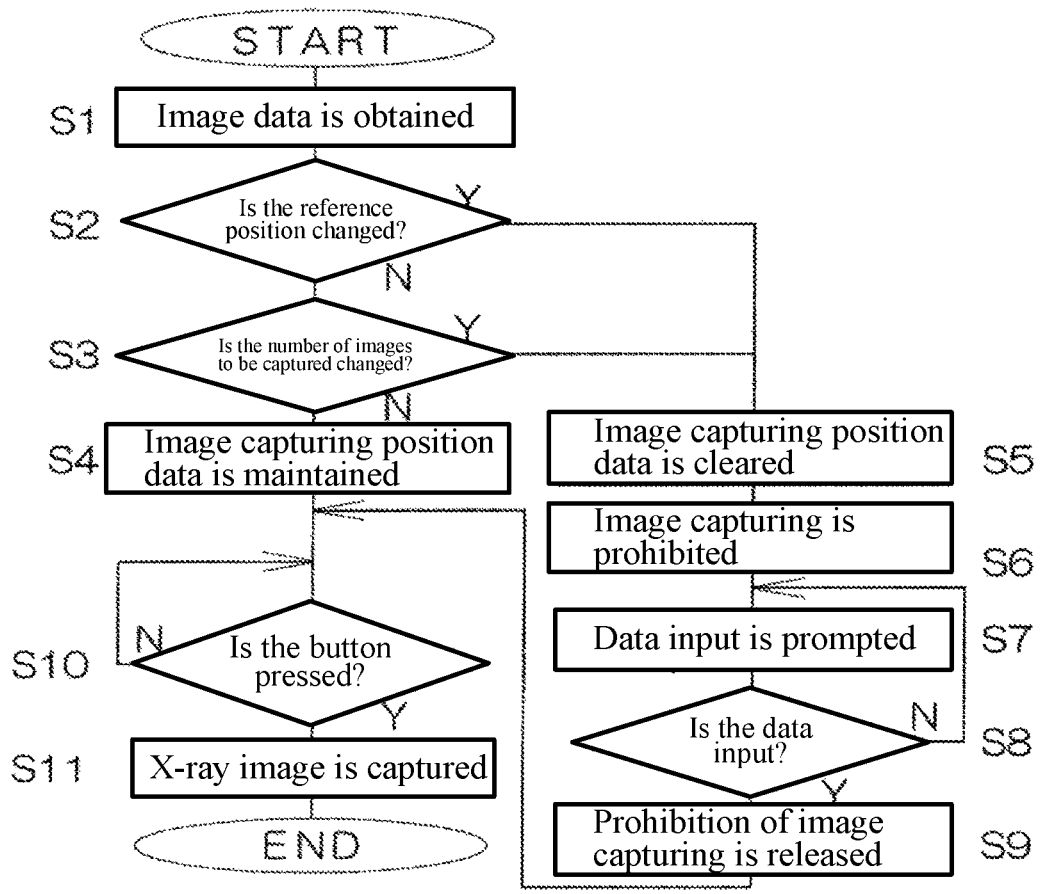
FIG. 5 is a flowchart showing an operation for continuously performing long-length image capturing by the X-ray image capturing apparatus according to the present invention.
Figure 7:
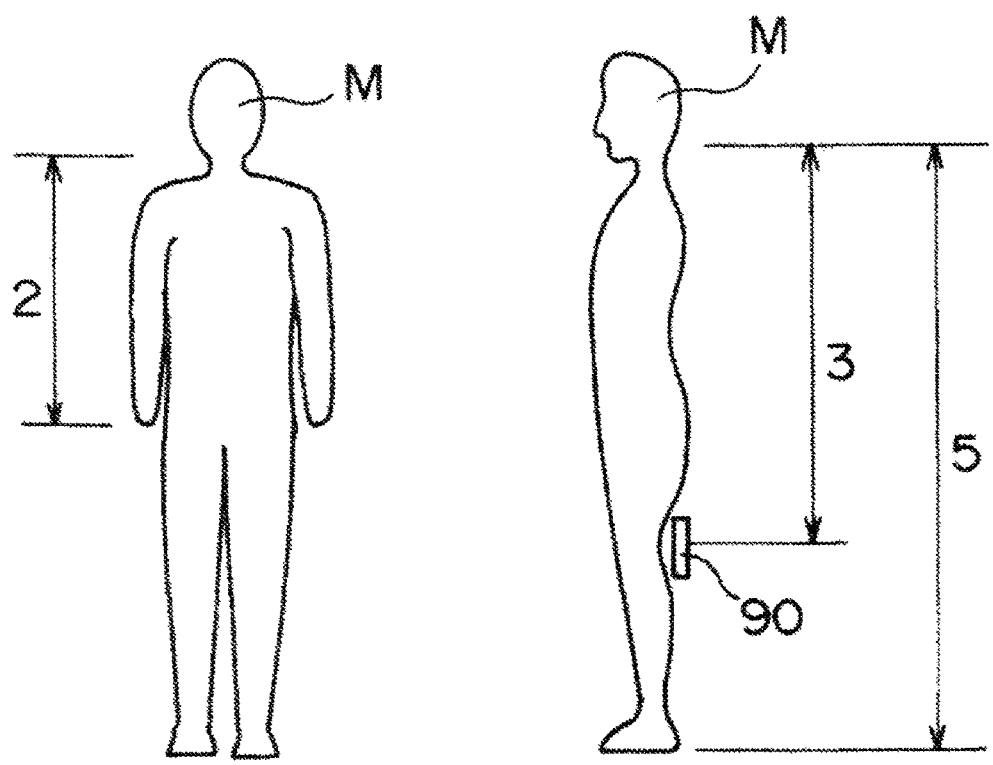
FIG. 7 is an explanatory view showing a state in which the number of images to be captured differs when performing image capturing from the front and when performing image capturing from the side.

Next, an image capturing operation in the case of continuously performing long-length image capturing by the X-ray image capturing apparatus having the aforementioned configuration will be described. FIG. 5 is a flowchart showing an operation of continuously performing long-length image capturing by the X-ray image capturing apparatus according to the present invention. Note that in the following description, an operation in a state in which first long-length image capturing has already been completed will be described.

First, image capturing data for performing long-length image capturing is acquired (Step S1). This image capturing data are various kinds of data for performing the long-length image capturing indicated by No. 1 to No. 5 in FIG. 6 in addition to various kinds of information of a subject M. At this time, the image capturing position data when the previous long-length image capturing was performed is stored in the image capturing position data storage unit 15 of the control unit 13.

Next, in order to perform the long-length image capturing, it is determined whether or not it is necessary to change the setting of the reference position of the long-length image capturing region (Step S2). In this case, in the previous long-length image capturing and the current long-length image capturing, it is determined whether or not there is a change between the entire spinal image capturing not adopting the lower reference indicated by No. 1 to No. 3 in FIG. 6 and the entire lower limb image capturing adopting the lower reference indicated by No. 4 and No. 5 in FIG. 6. When there is a change, the process proceeds to Step S5, and when there is no change, the process proceeds to Step S3.

In Step S3, it is determined whether or not there is a change in the number of images to be captured (Step S3). For example, in the previous long-length image capturing and the current long-length image capturing, it is determined whether or not there is a change between the entire spinal front image capturing in which the number of images to be captured is two (2) as indicated by No. 1 in FIG. 6 and the entire spinal side image capturing as indicated by No. 3 in FIG. 6. When there is a change, the process proceeds to Step S5, and when there is no change, the process proceeds to Step S4.

When there is no change in the setting of the reference position of the long-length image capturing region and no change in the number of images to be captured, the previous image capturing position data stored in the image capturing position data storage unit 15 of the control unit 13 is maintained (Step S4). That is, the next long-length image capturing is performed at the same image capturing position as in the previous long-length image capturing. For this reason, it becomes possible to efficiently perform the long-length image capturing by omitting unnecessary settings of image capturing positions at the time of performing the long-length image capturing. This makes it possible to shorten the time required for the long-length image capturing.

On the other hand, when either one of a change in the setting of the reference position of the long-length image capturing region and a change in the number of images to be captured is performed, the previous image capturing position data stored in the image capturing position data storage unit 15 of the control unit 13 is cleared (Step S5). Then, the control unit 13 once prohibits X-ray imaging (Step S6), and the warning display unit 16 displays on the display unit 11 a display prompting input of image capturing position data for the next long-length image capturing (Step S7). This display is performed until an operator inputs image capturing position data for the next long-length image capturing (Step S8). Note that the display prompting input of image capturing position data for the next long-length image capturing may be performed when the switch 23, which will be described later, is pressed.

When an operator inputs image capturing position data for the next long-length image capturing and this is stored in the image capturing position data storage unit 15 of the control unit 13, the control unit 13 releases the prohibition of image capturing (Step S9). That is, in the case of performing either entire spinal image capturing indicated by No. 1 to No. 3 in FIG. 6, an operator sets the upper end position and the lower end position of the image capturing region according to the height of the subject M. Also, in the case of performing the entire lower limb image capturing indicated by No. 4 or No. 5, the operator sets the upper end position of the image capturing region with the reference position as a lower position. The prohibition of image capturing is released when these data are stored in the image capturing position data storage unit 15.

Thereafter, it waits until the switch 23 of the high voltage equipment 2 is pressed (Step S10). When the switch 23 of the high voltage equipment 2 is pressed by the operator, a necessary number of X-ray image capturing is successively performed (Step S11). Then, the image processing unit 14 of the control unit 13 composes the plurality of captured images.

As described above, according to the X-ray image capturing apparatus as the radiation image capturing apparatus according to the present invention, unnecessary settings of image capturing positions are omitted and image capturing position settings are performed only when necessary. Therefore, it is possible to efficiently perform long-length image capturing. This increases the possibility that the time required for long-length image capturing can be shortened, which makes it possible to reduce the burden on both the operator and the subject M.

In the above-described embodiment, the configuration in which the X-ray tube 42 and the collimator 43 are swung by the swing drive unit 48 of the image capturing unit 4 in the direction facing the X-ray detection unit 33 is adopted. However, it is also possible to adopt a configuration in which the X-ray tube 42 and the collimator 43 are moved in the horizontal direction in synchronization with the movements of the X-ray detection unit 33.

In the above-described embodiment, the present invention is applied to the X-ray image capturing apparatus performing long-length image capturing for a subject M in the standing posture while moving the X-ray detection unit 33 in the standing posture image capturing stand 3 in the vertical direction. However, the present invention may be applied to an X-ray image capturing apparatus which performs long-length image capturing of a subject M in the lying posture.

DESCRIPTION OF REFERENCE SYMBOLS

1: console unit
2: high voltage equipment
3: standing posture image capturing stand
4: image capturing unit
11: display unit
12: operation unit
13: control unit
14: image processing unit
15: image capturing position data storage unit
16: warning display unit 22: operation panel
23: switch
32: ascending/descending drive unit
33: X-ray detection unit
42: X-ray tube
43: collimator
47: movement drive unit
48: swing drive unit
100: image capturing room
101: operation room
103: radiology department information system
M: subject

The invention claimed is:

1. A radiation image capturing apparatus equipped with a radiation detection unit configured to move along a body axis direction of a subject and a radiation irradiation unit configured to irradiate radiation toward the radiation detection unit, wherein the radiation image capturing apparatus is configured to perform long-length image capturing for creating a radiation image corresponding to a long-length image capturing region of a subject extending in a body axis direction of the subject by continuously performing image capturing a plurality of times to capture a plurality of images in which end portions thereof are overlapped and composing the plurality of images, characterized in that the radiation image capturing apparatus is configured to maintain image capturing position data indicating an upper end position or a lower end position of an image capturing region for first long-length image capturing when a setting of a reference position of the long-length image capturing region is not changed and the number of images to be captured are not changed after performing the first long-length image capturing and before performing second long-length image capturing, and is configured to clear the image capturing position data indicating an upper end position or a lower end position of an image capturing region for the first long-length image capturing and prohibit the second long-length image capturing until image capturing position data indicating an upper end position or a lower end position of an image capturing region for the second long-length image capturing is input when the setting of the reference position of the long-length image capturing region is changed or the number of images to be captured is changed after performing the first long-length image capturing and before performing the second long-length image capturing.

2. The radiation image capturing apparatus as recited in claim 1, wherein the radiation image capturing apparatus makes a display unit display a display prompting input of image capturing position data for the second long-length image capturing when the setting of the reference position of the long-length image capturing region is changed or the number of images to be captured is changed after performing the first long-length image capturing and before performing the second long-length image capturing.

3. The radiation image capturing apparatus as recited in claim 1, wherein a change of the setting of the reference position of the long-length image capturing region includes a change between a setting in which the reference position of the long-length image capturing region is set to a lower end portion of the subject and a setting in which the reference position of the long-length image capturing region is not set to the lower end portion of the subject.

4. The radiation image capturing apparatus as recited in claim 1, wherein the radiation detection unit is configured to move in a vertical direction and perform the first long-length image capturing and the second long-length image capturing of the subject in a standing position.

5. The radiation image capturing apparatus as recited in claim 2, wherein the radiation detection unit is configured to move in a vertical direction and perform the first long-length image capturing and the second long-length image capturing of the subject in a standing position.

6. The radiation image capturing apparatus as recited in claim 3, wherein the radiation detection unit is configured to move in a vertical direction and perform the first long-length image capturing and the second long-length image capturing of the subject in a standing position.

7. A method of image capturing with a radiation image capturing apparatus equipped with a radiation detection unit configured to move along a body axis direction of a subject and a radiation irradiation unit configured to irradiate radiation toward the radiation detection unit, comprising:

performing long-length image capturing for creating a radiation image corresponding to a long-length image capturing region of a subject extending in a body axis direction of the subject by continuously performing image capturing a plurality of times to capture a plurality of images in which end portions thereof are overlapped and composing the plurality of images;

maintaining image capturing position data indicating an upper end position or a lower end position of an image capturing region for first long-length image capturing when a setting of a reference position of the long-length image capturing region is not changed and the number of images to be captured are not changed after performing the first long-length image capturing and before performing second long-length image capturing; and clearing the image capturing position data indicating an upper end position or a lower end position of an image capturing region for the first long-length image capturing and prohibit the second long-length image capturing until image capturing position data indicating an upper end position or a lower end position of an image capturing region for the second long-length image capturing is input when the setting of the reference position of the long-length image capturing region is changed or the number of images to be captured is changed after performing the first long-length image capturing and before performing the second long-length image capturing.

8. The method of image capturing as recited in claim 7, further comprising providing a display prompting input of image capturing position data for the second long-length image capturing when the setting of the reference position of the long-length image capturing region is changed or the number of images to be captured is changed after performing the first long-length image capturing and before performing the second long-length image capturing.

9. The method of image capturing as recited in claim 7, wherein a change of the setting of the reference position of the long-length image capturing region includes a change between a setting in which the reference position of the long-length image capturing region is set to a lower end portion of the subject and a setting in which the reference position of the long-length image capturing region is not set to the lower end portion of the subject.

10. The method of image capturing as recited in claim 7, wherein the radiation detection unit is configured to move in a vertical direction and the method further comprises performing the first long-length image capturing and the second long-length image capturing of the subject in a standing position.

11. The method of image capturing as recited in claim 8, wherein the radiation detection unit is configured to move in a vertical direction and the method further comprises performing the first long-length image capturing and the second long-length image capturing of the subject in a standing position.

12. The method of image capturing as recited in claim 9, wherein the radiation detection unit is configured to move in a vertical direction and the method further comprises performing the first long-length image capturing and the second long-length image capturing of the subject in a standing position.

* * * * *